United States Patent
Axelgaard et al.

(10) Patent No.: US 6,788,979 B1
(45) Date of Patent: Sep. 7, 2004

(54) ELECTRICAL STIMULATION COMPRESS KIT

(75) Inventors: Jens Axelgaard, Fallbrook, CA (US); George Cornell, Ramona, CA (US); Steve Heard, Escondido, CA (US)

(73) Assignee: Axelgaard Manufacturing Co., Ltd., Fallbrook, CA (US)

(*) Notice: Subject to any disclaimer, the term of this patent is extended or adjusted under 35 U.S.C. 154(b) by 84 days.

(21) Appl. No.: 10/235,404

(22) Filed: Sep. 5, 2002

Related U.S. Application Data

(62) Division of application No. 10/171,703, filed on Jun. 14, 2002, which is a division of application No. 09/428,196, filed on Oct. 27, 1999, now Pat. No. 6,438,428.

(51) Int. Cl.⁷ .............................................. A61N 1/04
(52) U.S. Cl. ...................... 607/148; 607/149; 607/152; 607/153
(58) Field of Search ................................. 600/386, 390, 600/391, 393; 607/152, 149, 148, 153

(56) References Cited

U.S. PATENT DOCUMENTS

| | | | |
|---|---|---|---|
| 3,989,035 A | * 11/1976 | Zuehlsdorff | 600/391 |
| 5,336,255 A | * 8/1994 | Kanare et al. | 607/149 |
| 5,450,845 A | * 9/1995 | Axelgaard | 607/149 |
| 5,766,236 A | * 6/1998 | Detty et al. | 607/149 |
| 5,921,925 A | * 7/1999 | Cartmell et al. | 607/149 |

* cited by examiner

*Primary Examiner*—George R. Evanisko
(74) *Attorney, Agent, or Firm*—Walter A. Hackler

(57) ABSTRACT

An electrical stimulation device method provides for exact repeatable positioning of stimulation pads onto a body part. The device includes a flexible member for contacting a body part and hook/loop members for tightly supporting the flexible member against the body part. At least one electrical bus is provided which may include a connector for enabling connection of the bus to an electrical lead wire and an electrical contact disposed on the inside of the flexible member. A conductive pad is provided which has dimensions substantially smaller than the dimensions of the flexible member and includes a cover adhesive layer for removably adhering the conductive pad to the flexible member inside with a first side of the cover layer covering the bus contact and an electrical communication therewith. A current controlling media is adhered to a second side of the cover layer and a base layer disposed on the current controlling media is provided for removably adhering the conductive pad to the body part.

7 Claims, 2 Drawing Sheets

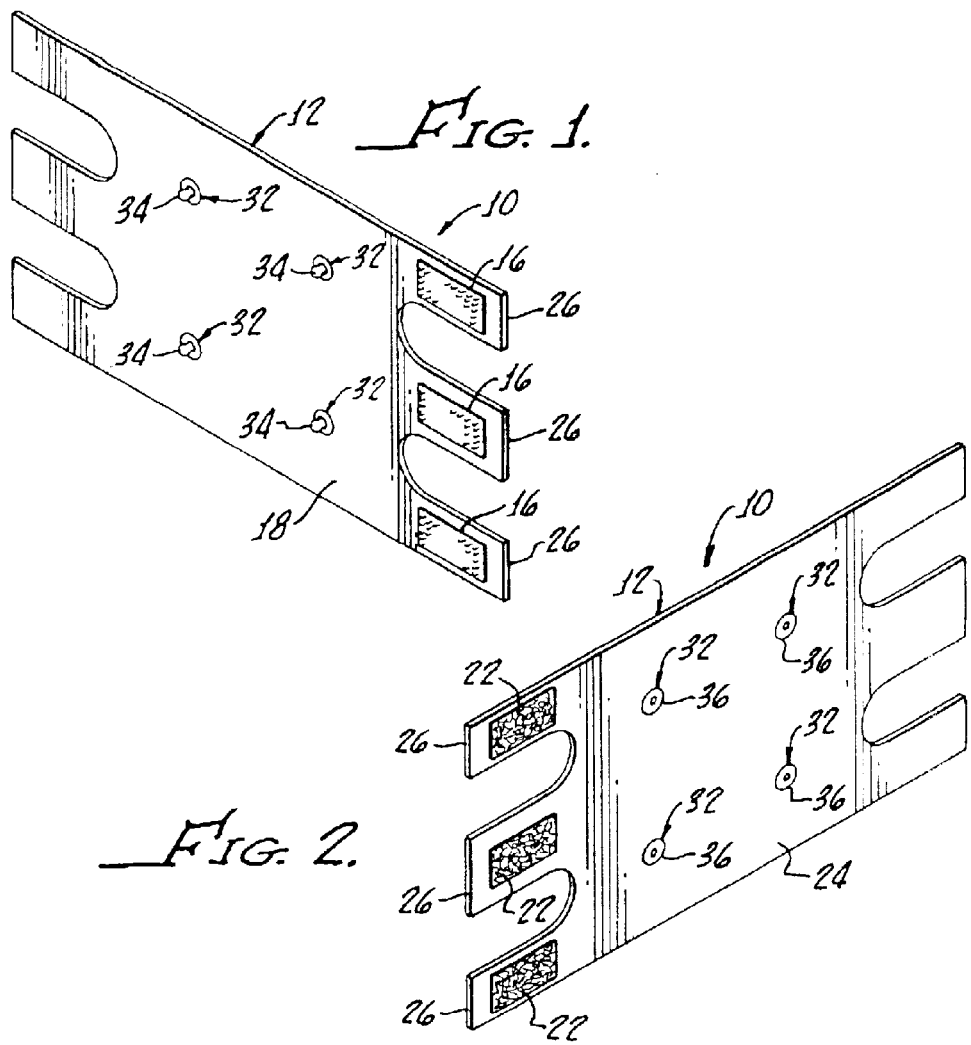
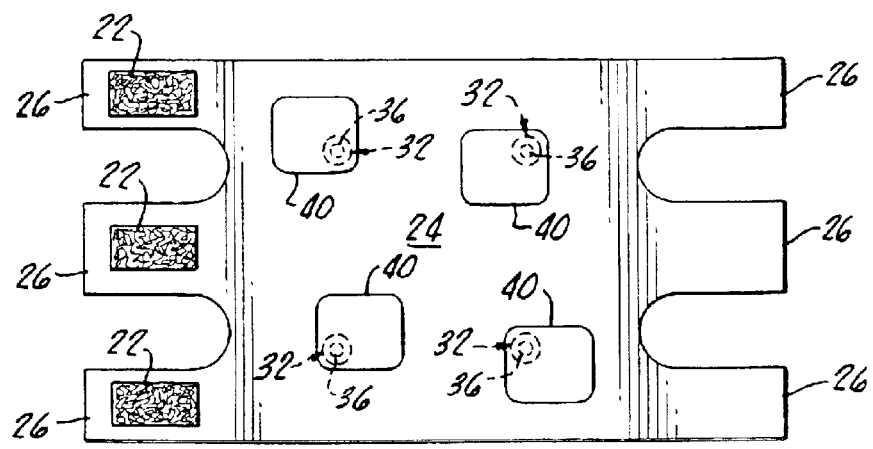

ELECTRICAL STIMULATION COMPRESS KIT

The present application is a division of U.S. patent application Ser. No. 10/171,703 filed on Jun. 14, 2002, now pending which is a division of U.S. patent application Ser. No. 09/428,196 filed on Oct. 27, 1999, now U.S. Pat. No. 6,438,428 issued Aug. 20, 2002.

Transcutaneous electrical nerve stimulation is used, for example, in post-operative and chronic pain control.

On the other hand, muscle stimulation is useful, for example, in maintenance and development of muscle tissue and is a particularly important function in sports medicine.

While significant advantages afforded through the use of electrical stimulation of nerves and muscles, its effectiveness can be enhanced when used in combination with a supporting compress, band or brace, which may not only provide for immobilization of the body part, but also proper placement and positioning of electrical stimulation electrodes with respect to the body part.

The use of stimulation electrodes necessarily mandates effective electrical coupling of the electrode to the skin. In order to accomplish this coupling, prior art devices have incorporated many types of conductive fluids and/or gels.

One type of electrode used for temporary application of muscle stimulation includes a flat, smooth contacting surface with a separate conductive cream or gel applied to the skin to electrically couple the electrode thereto. Experience with this system has shown that the cream and gel is messy to use and remove and the electrodes are not suitable for curved body parts. In addition, subsequent to use of the electrode, the cream or gel must be cleaned and washed from the skin and the electrode.

Another type of electrode more suitable for longer term application of electrical stimulation or monitoring includes a flexible conductive fabric or film material. In combination therewith, a conductive adhesive gel is utilized to perform a dual function of both electrically coupling the electrode to the body and adhering the electrode to the skin. While this type of electrode is effective, a great number of electrodes may be required to provide a long term treatment for certain conditions. When the electrodes are used in combination with a compress, band, brace gauntlet or other supporting garment or bandage, it is impractical to dispose of the supporting system due to loss of efficacy of the stimulation electrodes.

The present invention is directed to an electrical stimulation device which includes reusable compresses, bands, braces and the like, to a body part in which the electrical stimulation electrode is removably attached thereto.

This is accomplished in part through the use of electrical conductive pads, removably and electrically coupled to a compress or the like, which enables removable adherence to a body part.

A method encompassed by the present invention enables the precise placement of stimulation electrodes on a body part utilizing in combination electrical electrodes, or pads, with differential release adhesive thereon and a brace or compress.

SUMMARY OF THE INVENTION

An electrical stimulation device in accordance with the present invention for application to a body in part generally includes a flexible member for contacting a body part. The flexible member may have sufficient resiliency to act as a brace compress, splint or other function. Means are provided for tightly supporting the flexible member against the body part.

At least one electrical bus is provided which includes means, for enabling connection of the bus to an electrical lead wire. The bus also includes an electrical contact disposed on an inside of the flexible member.

A conductive pad is provided which has dimensions substantially smaller than dimensions of a flexible member. This enables the positioning of the conductive pad at one of an array of positions on the inside of the flexible member as long as it is placed in electrical communication with the contact on the inside of the flexible member.

A conductive pad generally includes cover electrically conductive gel adhesive layer means for removably adhering the conductive pad to the flexible member inside, with a first side of the cover layer means covering the bus contact and in electrical communication therewith.

A current controlling media is provided and adhered to a second side of the cover layer, and base electrically conductive gel adhesive layer means, disposed on the current controlling media, provides for removably adhering the conductive pad to the body part.

The electrical pad is, in fact, a multi-layer means, having differential release properties, for providing electrical interface between the patient's skin and the electrical bus. In this context, the multi-layer means includes a first layer (i.e., the base layer) comprising an electrically conductive gel having a relatively low peel strength, for removably contacting a body part, and a second layer means, (i.e., the cover layer), which comprises an electrically conductive gel having a relatively high peel strength, for contacting the flexible member inside and the electrical bus therein.

Thus, the cover layer means and the base layer means have adhesive properties enabling removal of the conductive pad from the body part by separation of the flexible member from the body part with the conductive pad remaining adhered to the flexible member during such separation. Subsequently, the pad may be removed from the flexible member inside surface and replaced due to the removable adhesive properties of the cover layer, or second layer means. Alternatively, as will be hereinafter discussed in greater detail, the adhesive properties of the layers may be selected in order that the flexible member may be removed with the pads remaining adhered to the body part.

In addition, the cover layer means and the base layer means may have adhesive properties enabling sliding of the conductive pad along the body part without separation of the conductive pad from the flexible member. This is important in positioning the device on the body. Thus, when the device is applied to the body, it may be moved into proper positioning which entails sliding the conductive pad along the body part without separation and misalignment of the conductive pad from the flexible member. The sliding property also facilitates placement, since adherence without the ability of translational movement, or sliding, would make placement of the device on a body part more difficult. Without the sliding property, the initial placement of the device on the body part would have to be exact. This, of course, does not allow for precise positioning of the electrical pads.

The device in accordance with the present invention may include a plurality of electrical busses disposed in a spaced apart relationship with one another in the flexible member and a plurality of conductive pads, each having dimensions substantially smaller than the flexible member dimensions. This arrangement allows for the exact relative positioning of pads with one another while at the same time allows a range of placement of each pad with respect to one another on the flexible member as long as each is utilized in contact with one of the busses. Thus, the flexible member can be uniformly made for use with patients having various size body parts, with the difference in size accommodated for by different spacing arrangements between the conductive pads on the flexible member.

The current controlling member may be a third gel, a conductive scrim, a conductive cloth, a conductive film or the like.

A method in accordance with the present invention for applying and positioning an electrical stimulation device on a body part generally includes the steps of removably adhering a plurality of conductive pads to a body part with a relative low peel strength electrically conductive layer. Thereafter, a flexible member is disposed onto the body part and removably adhered to the plurality of conductive pads with a lower peel strength layer. Each pad is electrically coupled to a respective electrical bus extending through the flexible member.

The body part is stimulated with electrical pulses and pads and the body part response to the electrical stimulation is determined.

The flexible member is removed from the body part and the conductive pads remain adhered to the body part. At least one of the conductive pads is removed and reapplied and the steps of disposing the flexible member onto the body part over the pads, electrical stimulation of the body part and a determination of the response to the electrical stimulation is repeated until a desired body part response is obtained.

Thereafter, a relatively high peel strength layer is applied to the conductive pads and the flexible member is disposed over the body part and adhered to the conductive pads with a relatively high strength adhesive.

This enables the pads to be removed from the body part with the flexible member.

The method further includes marking the flexible pads with the position of the conductive pads and, as necessary, replacing the conductive pads on the flexible member at the marked positions.

This method ensures proper relative placement of the conductive pads onto the body part for the most efficient muscle stimulation.

As an alternative, separate stimulation electrodes may be utilized in the method of the present invention. In this instance, a plurality of stimulation electrodes are removably adhered to a body part with a relatively low peel strength electrically conductive layer. The body part is then stimulated with the stimulation electrode and the body part response to the electrical stimulation is determined.

Thereafter, at least one of the stimulation electrodes is removed and reapplied and the steps of electrically stimulating the body and determining the response thereto is repeated until a desired body part response is obtained.

At that point, a flexible member is disposed onto the body part and removably adhered to the plurality of stimulation electrodes with a relatively high peel strength layer. The flexible member is removed from the body part with the stimulation electrodes adhered thereto.

The flexible member is then marked to indicate the positions of the stimulation electrodes thereon and the stimulation electrodes removed from the flexible member.

A plurality of conductive pads are then removably adhered to the marked positions on the flexible members with each pad being electrically coupled to a respective electrical bus in the flexible member. The flexible member is then disposed over the body part to removably adhere the conductive pads in positions corresponding to the stimulation electrodes.

BRIEF DESCRIPTION OF THE DRAWINGS

The advantages and features of the present invention will be better understood by the following description when considered in conjunction with the accompanying drawings, in which:

FIG. 1 is a perspective view of an outside of a flexible member in accordance with the present invention generally showing a means for tightly supporting the flexible member against a body part, not shown, along with a plurality of electrical busses;

FIG. 2 is a perspective view of an inside of the flexible member shown in FIG. 1, also showing cooperative means for tightly supporting the flexible member against a body part, also not shown in FIG. 2, as well as a reverse side of the electrical busses;

FIG. 3 is a plan view of the inside of the flexible member shown in FIG. 2 shown with a plurality of conductive pads placed thereon and removably adhered to the flexible member inside and in electrical contact with the busses.

DETAILED DESCRIPTION

Figures 4, 5, 6, 7:
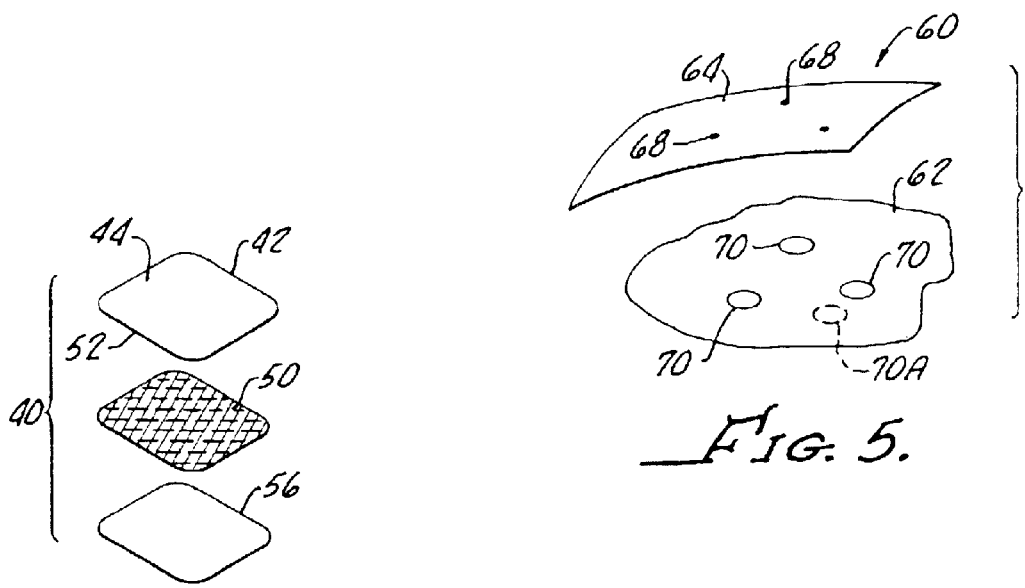
FIG. 4 is an exploded view of an electrical pad suitable for use with the flexible member shown in FIGS. 1–3 which, in combination therewith, provides for an electrical stimulation device in accordance with the present invention for application to a body part.
FIGS. 5–7 illustrate the method of the present invention.

With reference to FIGS. 1 and 2, there is shown an electrical stimulation device 10 for application to a body part (not shown) which generally includes a flexible member 12 for contacting a body part. The size and shape of the flexible member 12 may be varied considerably from that illustrated in the Figures of the present application, depending upon the body part to be contacted by the flexible member. It should be readily appreciated that the flexible member would have different dimensions and sizes for use on an arm, on a leg or other body part, the illustrated flexible member 12 being selected for use on a patient's limb, i.e., arm or leg.

It should also be appreciated that the material of construction of flexible member is varied as long as it is not electrically conductive. In fact, the stiffness of the member may be selected in order that the member 12 functions as a brace, a compress, bandage or other suitable application to a body part.

Micro hooks 16, disposed on an outside 18 of the flexible member (shown in FIG. 1) and micro loops 22 on an inside 24 of the flexible member 12 (shown in FIG. 2) attached to fingers 26 of the flexible member may provide a means for tightly supporting the flexible member against the body part (again not shown in the Figures).

A plurality of electrical buses 32 extend through the flexible member 12 and, on the outside 18, of the flexible member 12, include snaps 34, or the like which provides a means for enabling connection of the buses to one or more electrical lead wires, not shown.

On the inside 24 of the flexible member, each bus 32, includes an electrical contact 36 as shown in FIG. 2.

With reference to FIGS. 3 and 4, the present invention includes at least one, and preferably a plurality of conductive pads 40, having dimensions substantially smaller than the dimensions of the flexible member 12. This difference in overall dimensions between the pad 40 and flexible member 12, enables a variety of placement patterns, or arrays, of the conductive pads onto the inside 24 of the flexible member 12. This allows for precise alignment of the pads 40 onto a body part (not shown) and also to accommodate for patient having different sizes of body parts. The only limitation of placement of the pads 40 on the inside 24 of the flexible member 12 is the condition that the conductive pads 40 each cover a contact 36 of the electrical bus 32.

With specific reference to FIG. 4, each conductive pad 40 includes a cover electrically conductive gel adhesive layer 42 which provides a means for removably adhering the conductive pad 40 to the flexible member inside 24 with a first side of the cover layer covering the bus contact 36 and in electrical communication therewith.

A current controlling media 50 is adhered to a second side 52 of the gel layer 42. This conductive media may be of a number of configurations including a metal scrim, or a conductive gel, a conductive fabric, a conductive film, or a conductive film with conductive traces, as is well known in the art. See U.S. Pat. No. 5,904,712.

The pad 40 further includes a base electrically conductive gel adhesive layer 56 disposed on the current controlling conductive media 50 which provides a means for removably adhering the conductive pad 40 to the body part.

Thus, the conductive pad 40 is, in fact, a multi-layer means for providing an electrical interface between the body part and the electrical bus 32 with the multi-layer means including a first layer, or as hereinabove designated, a base layer 56 comprising an electrically conductive gel having a relatively low peel strength for removably contacting the body part, and a second layer, hereinabove referred to as the cover layer 42, comprising an electrically conductive gel having a relatively high peel strength, for contacting the flexible member inside and contacting the electrical bus 32.

Thus, the cover, or second, layer 42 and the base, or first, layer 56 have adhesive properties enabling removal of the conductive pad 40 from the body part by separation of the flexible member 12 from the body part, with the conductive pad 40 remaining adhered to the flexible member inside 24 during such separation. Accordingly, the flexible member can be applied and removed to the body part without disturbing the relative placement of the pads 40 on the flexible member inside surface 24.

Further, the cover or second, layer 42 and the base, or first, layer 56 may have adhesive properties enabling sliding of the conductive pad 40 across a body part without separation of the conductive pad 40 from the flexible member 12. Importantly, as hereinabove noted, this feature enables the device 10 to be properly fixed to the body part by the hook 16 and loops 22 by exactly positioning the pads 40 to desired locations without complete removal of the device 10 from the body part and reapplication.

All of the layers 42, 50, 56 of the pad 40 are described in U.S. patent application Ser. No. 09/021,009, now U.S. Pat. No. 6,038,464, entitled MEDICAL ELECTRODE AND METHOD OF MANUFACTURE. This referenced U.S. Pat. No. 6,038,464, is totally incorporated herein by this specific reference thereto including all drawings and specifications for teaching a person skilled in the art how to make and use the conductive pads 40 in accordance with the present invention.

Further description of the conductive organic polymers that may be used in preparing the layers 42, 56 may be derived from the copolymerization of a mixture of monomeric acrylic acid and N-vinyl-pyrollidone. These polymers are set forth in U.S. Pat. No. 5,868,136, which is to be incorporated herewith in its entirety including all drawings and specification to describe generally suitable polymers.

With reference to FIGS. 5–7, there is illustrated a method in accordance with the present invention for applying and positioning an electrical stimulation device 60 onto a body part 62.

As is well known in the art, stimulation electrodes must be accurately placed on a body part in order to ensure effective stimulation. This is particularly true when multiple electrodes are utilized. Unfortunately, the precise placement of the electrodes is not easily accomplished by a patient utilizing a stimulation device over a long period of time. While a qualified physician or attendant can properly place electrodes on a patient's body, such procedures are not amenable to long term use in which the electrodes are replaced. The present invention enables the device 60 to be utilized by a patient with repeated applications and changes of electrodes while maintaining the precise positioning of the electrodes with respect to the body parts to effect efficient stimulation.

As illustrated in FIGS. 5–7, the flexible member 64 which may be, identical to the flexible member 12 hereinabove described, includes a plurality of buses 68 therethrough, also hereinabove described.

As shown in FIG. 5, the method includes removably adhering a plurality of conventional stimulation electrodes, or pads 70 to a body part with a relatively low peel strength electrically conductive layer as hereinabove discussed in connection with the pads 40. Thereafter, the electrodes, or pads 70 may be separately electrified to stimulate the body part 62 and the body part response to such electrical stimulation is determined in a conventional manner.

Thereafter, one of the stimulation electrodes 70 may be removed and reapplied as indicated by the dashed line 70A in FIG. 5. The body part is again electrically stimulated with the electrodes 70, 70A and the body part response is determined. This procedure is repeated until a desired body part response is obtained.

Thereafter, the flexible member 64 is disposed onto the body part 62 and removably adhered to the electrode 70, the adherence being made with a relatively high peel strength layer.

As shown in FIG. 6, the flexible member 64 is removed with the electrodes 70 adhered thereto.

The positions of the electrodes 70 are then marked onto the flexible member 64 and replaced with conductive pads 40 which are in contact with the electrical busses 68 in the flexible member 64. Because the flexible member 64 is marked, repeated replacement of conductive pads 40 (not shown in FIGS. 5–7) with precise relative spacing is enabled. Thus, a patient can replace conductive pads and reapply the device 60 while ensuring proper placement of the pads 40 onto the body part 62.

As hereinabove described, the stimulation electrodes 70 may be replaced by the conductive pads 40 after placement of the electrode 70 onto the body part 64 is determined.

Alternatively, the conductive pads 40 themselves may be used to determine the exact placement.

In this procedure, a plurality of conductive pads 40 are removably adhered to the body part 60 with a relatively low peel strength electrically through a conductive layer. The flexible member 64 is disposed on the body part 62 and removably adhered to the plurality of conductive pads 40 with a low peel strength layer, each pad 40 being electrically coupled to a respective bus 68 extending through the flexible member 64.

The body part is electrically stimulated with electrical pulses applied through the buses 68 and pads 40. The body part 62 response is determined and the flexible member 64 is removed from the body part with the conductive pads 40 remaining adhered to the body part 62. At least one of the conductive pads 40 is removed and reapplied and the steps of stimulation and determination of body response are repeated until a desired body part response is obtained.

Thereafter, a relatively high peel strength layer is applied to the conductive pads adhered to the body part and the flexible member 64 is disposed onto the body part and adhered to the flexible member with the relatively high peel strength adhesive.

Thus, the use of adhesive layers having relatively high peel strength which provide a differential release enables the performance of the method in accordance with the present invention.

In accordance with the present invention, the conductive pads 40 may be adhered to the flexible member 64 with a relatively high peel strength layer and adhered to the body part with a relatively low peel strength layer to enable repeated disposal and removal of the flexible layer 64 to the body part 62 without disturbing the relative positioning of the conductive pads adhered thereto.

Alternatively, the conductive pads 40 may be adhered to the flexible member 64 with a relatively low peel strength layer and adhered to the body part with a relatively high peel strength layer to enable the conductive pads to remain adhered to the body part 62 when the flexible member 64 is removed from the body part 62. This enables repeated application of the flexible member and replacement of the conductive pads 40 thereon through the use of the markings on the flexible member 64 indicating the proper positioning of the conductive pads 40 thereon.

In a further embodiment of the method in accordance with the present invention, a patient may be stimulated with electrodes 70 that are moved until the desired response is obtained. Then the patient's skin is marked with an easily removable marker where the electrodes are placed. The standard stimulation electrodes 70 are then replaced with the conductive pads 40 using the marks as guidance. The flexible member 64 is then placed over the pads 40 in its optimum position. The flexible member 64 is removed with the pads 40. The outline of the pads 40 is marked with a permanent marker on the inside of the flexible member 64 for future reference. The flexible member is ready for use. The pads 40 can be replaced as desired by using the marked reference outlines for correct and accurate placement. This can be done by the patient since no further pad adjustment is necessary to effect proper stimulation.

Although there has been hereinabove described a specific embodiment of the present invention for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope of the present invention as defined in the appended claims.

What is claimed is:

1. An electrical stimulation kit for application to a body part, the device comprising:

a flexible member for contacting a body part, said flexible member having an electrical contact disposed on an inside of said flexible member;

means for tightly supporting said flexible member against the body part;

an electrical bus disposed in said flexible member for enabling electrical connection to said electrical contact through said flexible member; and at least one electrode selected from a group consisting of:

a first electrode, disposable between said flexible member and said body part, for providing an electrical interface between said body part and the bus, said first electrode including a first layer comprising an electrically conductive gel having a relatively high peel strength for removably contacting said body part and a second layer comprising an electrically conductive gel having a relatively low peel strength for contacting said flexible member and said electrical contact, the relative peel strengths enabling removal of said flexible member from said body part leaving said first electrode adhered to said body part;

a second electrode, disposable between said flexible member and said body part, and for providing an electrical interface between said body part and the bus, said electrode including a first layer comprising an electrically conductive gel having a relatively low peel strength for removably contacting said body part and a second layer comprising an electrically conductive gel having a relatively high peel strength for contacting said flexible member and said electrical contact, the relative peel strengths enabling removal of said second electrode from said body part by separation of said flexible member from said body part, said second electrode remaining adhered to said flexible member during separation from said body part; and a plurality of electrical buses disposed in a spaced apart relationship with one another in said flexible member, and a plurality of said first and second electrodes each having dimension substantially smaller than flexible member dimensions.

2. The kit according to claim 1 wherein the relative peel strengths of the second electrode first and second layer enable sliding of said second electrode along said body part without separation of said second electrode from said flexible member.

3. The kit according to claim 1 wherein said flexible member has sufficient resiliency to act as a brace for said body part.

4. The kit according to claim 1 wherein each electrode has sufficient conductivity to enable efficient electrical coupling between the buses and said body part independent of placement of each electrode on said flexible member inside, as long as each electrode covers a respective bus contact.

5. The kit according to claim 1 wherein each electrode comprises a current controlling media.

6. The kit according to claim 5 wherein said current controlling media comprises a scrim.

7. The kit according to claim 5 wherein said current controlling media comprises a third gel.

* * * * *